United States Patent [19]

Rosenberg

[11] Patent Number: 4,701,162
[45] Date of Patent: Oct. 20, 1987

[54] FOLEY CATHETER ASSEMBLY

[75] Inventor: Philip Rosenberg, Gurnee, Ill.

[73] Assignee: The Kendall Company, Boston, Mass.

[21] Appl. No.: 779,751

[22] Filed: Sep. 24, 1985

[51] Int. Cl.⁴ .............................................. A61M 25/00
[52] U.S. Cl. ...................................... 604/103; 604/283
[58] Field of Search ................... 604/103, 96, 284, 283

[56] References Cited

U.S. PATENT DOCUMENTS 4,207,899  6/1980  Patel .................................... 604/103
4,222,384  9/1980  Birtwell .............................. 604/103

Primary Examiner—Stephen C. Pellegrino
Attorney, Agent, or Firm—Donald N. Halgren

[57] ABSTRACT

A shaft and a connector with a side arm which when assembled comprise a catheter. The connector has an inflation lumen in its side arm and an axial bore through the body of the connector, the inflation lumen and the bore being in fluid communication.

The bore has three annular channels therein. Two of the channels are arranged to receive adhesive through the wall of the connector, and the third channel is intermediate the other two is in fluid communication with the inflation lumen of the side arm. The shaft has a drainage lumen and an inflation lumen therein. A pair of openings to the inflation lumens, are disposed in the shaft, corresponding to two of the channels in the connector.

Adhesive injected into the outer channels bonds the shaft to the connector and seals the proximalmost orifice of the inflation lumen in the shaft. The other opening provides fluid communication between the inflation lumen of the shaft and the inflation lumen of the side arm.

10 Claims, 4 Drawing Figures

U.S. Patent  Oct. 20, 1987  4,701,162
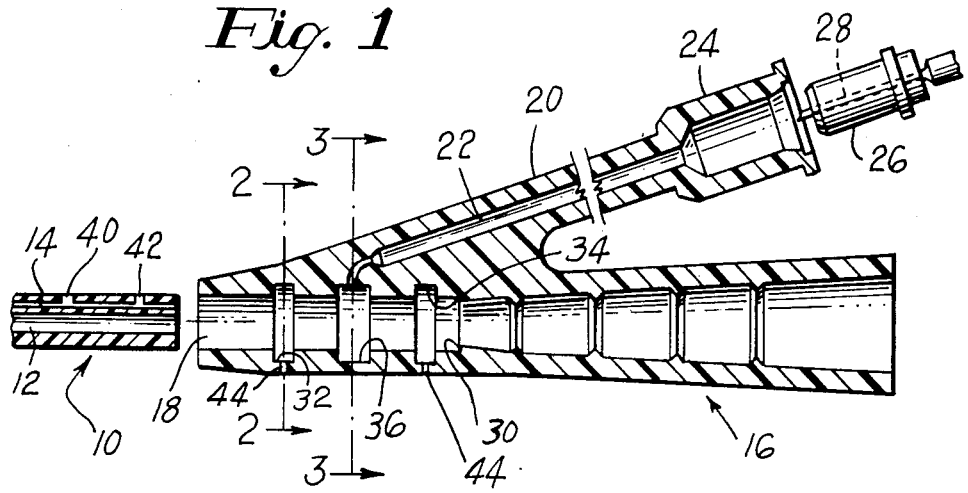
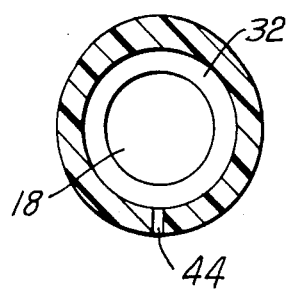 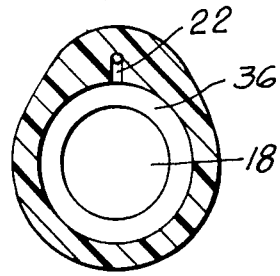
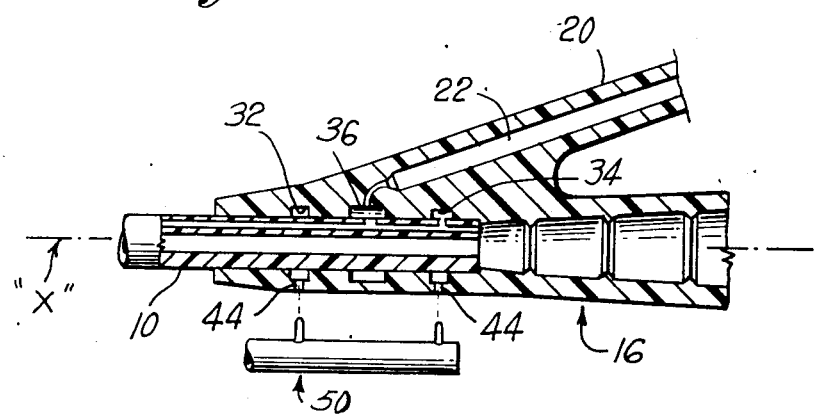

FOLEY CATHETER ASSEMBLY

FIELD OF THE INVENTION

This invention relates to catheters, and more particularly to catheter assemblies and their method of manufacture.

PRIOR ART

Foley catheters are commonly constructed with a shaft having a drainage lumen and an inflatable balloon adjacent the distal end of the shaft. During placement, the distal end of the catheter is passed through the patient's urethra until the balloon and drainage eyes, which communicate with a drainage lumen, are located in the patient's bladder, and the balloon is inflated through an inflation lumen to retain the catheter in place. During catheterization, urine drains through the drainage eyes and lumen and through a drainage tube connected to a proximal end of the catheter to a drainage bag for collection therein.

Conventional catheters of this sort were made from latex rubber through dipping techniques known to the art. In time, it was discovered that latex catheters were not completely satisfactory. As a result, it became desirable to construct the catheter shaft from a material which may be extruded in order to prevent possible blockage of the inflation lumen, and reduce the cost of the catheter to the patient due to simplified manufacturing techniques.

In turn, the materials which appeared satisfactory for use as the shaft posed new problems in construction of the catheter. For example, it became necessary to find suitable materials for the balloon which are sufficiently elastic to permit inflation during use, and which are compatible with the selected shaft for bonding purposes. Frequently, materials which appeared otherwise satisfactory for the catheter shaft and balloon proved to be incompatible when attempts were made to bond the balloon to the shaft through use of adhesive or sealing. In addition, it became necessary to secure a tip to the distal end of the extruded shaft, and the connector to the proximal end of the shaft. Such tips and connectors have been formed separately, and have been adhered to the shaft. In the case of the tips, it is necessary only to obtain a sufficient bond of the tip to the distal end of the shaft while closing the distal end of the inflation lumen. However, in the case of the connectors, it is necessary to establish communication between lumens in the connector in the associated inflation and drainage lumens in the shaft. Difficulties have been encountered in obtaining the proper alignment of lumens and achieving the desired bond. In addition, it is necessary in the past to separately form an opening in the outer space of the shaft to obtain communication between the inflation lumen and a cavity beneath the balloon. All of the excessive operations and difficulties associated with construction of the catheter deleteriously effect the capability of providing the catheter, which is considered a disposable item, at a significantly reduced cost.

U.S. Pat. No. 4,335,723 to B. C. Patel, shows a catheter assembly manufactured by a flexible shaft attached to a connector having an adapter tube arranged therein between. The adapter tube is hollow and has a flange at one end thereof. The adapter tube, the shaft and the connector are all bonded together after careful alignment thereof.

U.S. Pat. No. 4,284,459 to B. C. Patel, et al., shows a method of making a molded catheter wherein an elongated shaft having a main lumen extending therethrough and an inflation lumen extending through the wall of the shaft is molded directly onto a connector on the proximal end of the shaft.

U.S. Pat. No. 3,602,228 to C. C. Cowley shows a Y-connector on a catheter assembly with an annular recess in communication with its inflation funnel. The catheter is "welded or cemented therein", showing no recognition of an assembly problem or a solution therefor, by which annular channels on each side of the inflation channel is used to secure the catheter to the connetor and to seal the proximalmost end of the inflation lumen in the catheter.

It is an object of the present invention to provide a catheter which is relatively more simple and inexpensive to manufacture than the aforementioned prior art.

It is a further object of the present invention to provide a catheter assembly wherein the rotational orientation of the shaft is immaterial with respect to the molded "Y" connector to facilitate assembly thereof.

It is yet a further object of the present invention to provide a method of assembling a catheter with a minimum of labor.

BRIEF SUMMARY OF THE INVENTION

The present invention comprises a Y-shaped molded connector having a continuous passage axially disposed therethrough. The connector has a branch angularly disposed thereon, the branch having a channel disposed therethrough which is in fluid communication with the axially disposed passage of the connector. The connector is arranged so as to receive an extruded shaft, having a continuous central passageway or drainage lumen and a smaller inflation lumen. The connector is arranged so as to receive the extruded shaft therein. The extruded shaft has a proximal end which abuts against an angular shoulder in the continuous passageway of the connector. At least three annular channels may be transversely disposed within the continuous passageway of the connector distally of the shoulder. The intermediate channel is in fluid communication with the passageway arranged in the branch of the connector and may extend in an arc of about 180° to 270° or it may be a completely annular channel. The other two annular channels each have an opening disposed generally radially outwardly therefrom through the connector wall. The extruded shaft has a radially extending orifice which permits fluid communication between the inflation lumen thereof and the intermediate annular channel of the connector when the extruded shaft is disposed therewithin. A further orifice is disposed between the aforementioned orifice and the closest end of the extruded shaft, permitting fluid communication again, however, it is between the inflation lumen and the proximal annular conduit of the connector. Adhesive may be supplied through proper means through the radially directed conduits to the outside annular channels adjacent the extruded shaft in the continuous passageway of the connector. By rotating the extruded shaft at least through 360° as the adhesive is being applied into the annular channels, the adhesive is being spread on the outer periphery of the extruded shaft at two parallel peripheral locations, thus providing securement for the extruded shaft within the connector and providing sealing means against leakage for the inflation lumen. Additionally, as the extruded shaft is rotated, adhesive is also caused to be disposed into an upstream orifice which is cut in through the wall of the extruded shaft and into the inflation lumen near the proximal end of the shaft to provide sealant thereof at its upstream end. The orifice radially adjacent to the annular channel which is in communication with the channel in the branch of the connector permits fluid communication between the inflation lumen of the branch with the inflation lumen of the extruded shaft. Thus the extruded shaft may be disposed into the connector during assembly of the catheter with only regard to ensuring fluid communication between the inflation lumen and the 270° channel, if that embodiment is used, or without regard for its angular positioning since the intermediate annular channel will always be in fluid communication with the inflation lumen of the extruded shaft, if that 360° embodiment is utilized while the shaft itself is secured in the connector at two circumferential locations and the proximal end of the inflation lumen is sealed with adhesive through its radial notch, all of which is accomplished in a short operation.

BRIEF DESCRIPTION OF THE DRAWINGS

The objects and advantages of the present invention will become more apparent when viewed in conjunction with the following drawings in which;

FIG. 1 is a side elevational view in partial section, showing an extruded shaft before it is assembled with a connector;

FIG. 2 is a view taken along the lines II—II of FIG. 1;

FIG. 3 is a view taken along the lines III—III of FIG. 1; and

FIG. 4 is a side elevational view in partial section showing an extruded shaft assembled with a connector.

DESCRIPTION OF THE PREFERRED EMBODIMENT

Referring now to the drawings in detail, and particularly to FIG. 1, there is shown a portion of a catheter shaft 10 having a drainage lumen 12 an an inflation lumen 14. The distal portion of the shaft 10, as shown in the drawings, may be of conventional construction and adapted to be inserted into a body cavity and having an eye opening to the drainage lumen for collection of fluid from the cavity and having an inflatable retention balloon surrounding the shaft and in communication only with the inflation lumen, as shown in U.S. Pat. No. 4,342,316, assigned to The Kendall Company, and incorporated herein by reference.

The proximal portion of the shaft 10, as shown in FIG. 1, is insertable into the distal portion of a connector 16, or "Y", as shown in FIG. 4. The connector 16 is a flexible resilient or elastic one-piece molded unit having an axially disposed drainage bore 18 extending therethrough. The connector 16 also comprises an inflating side arm 20 angularly arranged on the side of the connector 16. The side arm 20 has an inflation lumen 22 which is in fluid communication with the drainage bore 18. The side arm 20 has an outer end 24 which may have a combination filling plug and closure 26 or check valve disposed therein. A hypodermic needle and barrel 28 may be used as an inflation means by passing the needle through the filling plug and closure 26.

The drainage bore 18 is arranged so as to receive the proximal end of the catheter shaft 10, to a shoulder 30 which acts to prevent further advance of the catheter shaft 10 into the drainage bore 18.

A pair of annular sealing channels 32 and 34 are transversely disposed about the periphery of the drainage bore 18, as shown in FIGS. 1 and 4. A third channel 36 is disposed intermediate the annular sealing channels 32 and 34 in the bore 18 of the connector 16. The third channel 36 is in fluid communication with the inflation lumen 22 of the side arm 20. The third channel 36 extends at least 270° around the internal periphery of the drainage bore 18, the mid-point of the channel 36 defining the locus of fluid communication between the intermediate third channel 36 and the inflation lumen 22. Preferably, the third channel 36 extends the full 360° around the internal periphery of the drainage bore 18, so as to maximize the likelihood of fluid communication between the inflation lumen 14 of the catheter shaft 10 and the third channel 36.

A first orifice 40 is disposed in the sidewall of the catheter shaft 10 to provide an opening only to the inflation lumen 14 therein. The first orifice 40 is spaced from the proximal end of the catheter shaft 10 so as to be in radial alignment with the third channel 36 in the drainage bore 18, as shown in FIG. 3.

A second orifice 42 is also disposed through the sidewall of the catheter shaft 10 to provide an opening to the inflation lumen 14 therein, and be in radial alignment with the proximalmost sealing channel 34 in the drainage bore 18.

Each sealing channel 32 and 34 has a generally radially directed conduit 44 which is disposed through the wall of the connector 16. The cross-sectional view shown in FIG. 2 is typical of both sealing channels 32 and 34.

Assembly of the shaft 10 and the connector 16 is accomplished by insertion of the proximal end of the shaft 10 into the drainage bore 18, to the point where the first orifice 40 in the sidewall of the inflation lumen 14 is in radial alignment with intermediate (inflating) channel 36, and the second orifice 42 is in radial alignment with the proximalmost annular channel 34. An adhesive dispensing means 50, is inserted into each conduit 44 leading to each sealing channel 32 and 34. A charge of adhesive is injected into each sealing channel 32 and 34 and the catheter 10 may be rotated at least 360° about its longitudinal axis "x". The "drag" of the outside wall of the catheter 10 on the adhesive pulls it therearound so as to help wrap a full circumferential bead of adhesive in the sealing channels 32 and 34 around the catheter shaft 10, thus sealing up the intermediate channel against leakage therefrom as well as securing the catheter 10 in the connector 16. As the adhesive is filling the proximalmost channel 34, it is also caused to enter the second orifice 42 adjacent the the end of the shaft 10, sealing the proximal end of the inflation lumen 14 thereby.

Thus there has been shown a novel catheter apparatus and method of assembling that apparatus in a simple and inexpensive manner, whereby exacting engagement of subcomponents is not necessary, thus permitting an efficient assembly thereof, while not minimizing or effecting the capability of the catheter assembly in any way.

I claim:

1. A catheter assembly comprising a shaft having a drainage lumen and an inflation lumen mateable with a connector with a generally axially disposed bore therethrough and an inflation side arm, said connector comprising:

an inflation means which provides fluid communication between said inflation side arm and said inflation lumen in said shaft, in any rotational orientation of said shaft; and a rotatively enactable sealing means disposed about said bore for securing said shaft in said bore of said connector and for preventing leakage of fluid from said inflation means;

said sealing means comprising at least one annular channel having means for the receipt of adhesive, said channel disposed in said bore radially outwardly of said shaft.

2. A catheter assembly as recited in claim 1, wherein said sealing means has a conduit thereto disposed through the wall of said connector in fluid communication with said annular channel arrangement.

3. A catheter assembly as recited in claim 1, wherein said inflation means comprises an inflation channel in said bore which inflation channel is in fluid communication with said inflation arm.

4. A catheter assembly as recited in claim 3, where said inflation means also comprises an orifice disposed through the wall of said shaft to said inflation lumen to provide fluid communication thereto.

5. A catheter assembly as recited in claim 3, wherein said inflation channel describes an arc of about 270° in said bore of said connector.

6. A method of assembling a shaft and a connector having a bore therethrough, to manufacture a catheter assembly, comprising the steps of:

providing a shaft having a drainage lumen and an inflation lumen therethrough, with at least two orificii through the outer wall of said inflation lumen;

inserting said shaft into said bore of said connector, said bore having at least two annular sealing channels and an inflation channel spaced between said sealing channels;

securing said shaft to said connector;

aligning one of said orificii with said inflation channel and another orifice with one of said sealing channels; and injecting an adhesive through an orifice arrangement in said connector to drive said adhesive into said sealing channels.

7. A catheter assembly as recited in claim 1, wherein said sealing means comprises at least two annular sealing channels disposed in said bore in said connector, at least one of said annular sealing channels being longitudinally disposed on each side of said inflation means.

8. A catheter assembly as recited in claim 7 wherein said sealing means also comprises an orifice through the wall of said shaft into said inflation lumen, said orifice providing fluid communication to said adhesive to the proximalmost of said annular sealing channels.

9. A method of assembling a shaft and a connector to manufacture a catheter assembly as recited in claim 6, including the steps of:

rotating said shaft about its longitudinal axis so as to distribute the adhesive throughout said sealing channels and the entire circumference of said shaft to provide full 360° sealing of said shaft to said bore and prevent leakage therepast from said inflation channel.

10. A method of assembling a shaft and a connector to manufacture a catheter assembly as recited in claim 6, including the steps of:

filling up the proximalmost orifice in the wall of said shaft with adhesive as said shaft is rotated on its longitudinal axis, thus further preventing leakage therefrom.

* * * * *